United States Patent
Barmettler et al.

(10) Patent No.: US 10,241,123 B2
(45) Date of Patent: Mar. 26, 2019

(54) LABORATORY INSTRUMENT AND METHOD OF USING THE SAME

(71) Applicant: Roche Molecular Systems, Inc., Pleasanton, CA (US)

(72) Inventors: Kurt Barmettler, Lucerne (CH); Andre Peter, Meggen (CH)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 0 days.

(21) Appl. No.: 15/364,048

(22) Filed: Nov. 29, 2016

(65) Prior Publication Data

US 2017/0153260 A1 Jun. 1, 2017

(30) Foreign Application Priority Data

Nov. 30, 2015 (EP) ..................................... 15197007

(51) Int. Cl.
*G01N 35/00* (2006.01)
*G01N 35/02* (2006.01)
(Continued)

(52) U.S. Cl.
CPC ....... *G01N 35/026* (2013.01); *G01N 35/0099* (2013.01); *G01N 35/00732* (2013.01); *G01N 35/1002* (2013.01); *B01L 3/021* (2013.01); *G01N 2035/00752* (2013.01); *G01N 2035/00782* (2013.01); *G01N 2035/0412* (2013.01);
(Continued)

(58) Field of Classification Search
CPC .......... G01N 2035/00752; G01N 2035/00782; G01N 2035/0412; G01N 2035/0413; G01N 2035/1051; G01N 35/00732; G01N 35/0099; G01N 35/026; G01N 35/1002
See application file for complete search history.

(56) References Cited

U.S. PATENT DOCUMENTS

| 5,948,360 A | 9/1999 | Green et al. | |
|---|---|---|---|
| 2002/0164269 A1* | 11/2002 | Ngo | G01N 35/026 422/63 |

(Continued)

FOREIGN PATENT DOCUMENTS

| CN | 202153227 U | 2/2012 |
|---|---|---|
| CN | 203929791 U | 5/2014 |

(Continued)

OTHER PUBLICATIONS

Extended Search Report for EP15197007.6, dated Jun. 17, 2016.

*Primary Examiner* — Jennifer Wecker
(74) *Attorney, Agent, or Firm* — Eric Grant Lee; Pamela C. Ancona

(57) ABSTRACT

Disclosed is a method of operating a laboratory instrument (100, 1000), wherein the laboratory instrument is configured for receiving a sample rack (112) with one or more sample tubes (126), wherein the laboratory instrument comprises a robotic head (106) for bringing a pipettor (108) into fluidic contact with the one or more sample tubes when the sample rack is in an operating position (122), wherein the robotic head is configured for loading the sample rack into the operating position, and wherein the method comprises the steps of: receiving (200) the sample rack by the laboratory instrument; and loading (202) the rack into the operating position using the robotic head.

16 Claims, 13 Drawing Sheets

(51) Int. Cl.
*G01N 35/10* (2006.01)
*B01L 3/02* (2006.01)
*G01N 35/04* (2006.01)

(52) U.S. Cl.
CPC ............. *G01N 2035/0413* (2013.01); *G01N 2035/1051* (2013.01)

(56) References Cited

U.S. PATENT DOCUMENTS

| | | |
|---|---|---|
| 2004/0047765 A1 | 3/2004 | Grodon et al. |
| 2006/0263248 A1 | 11/2006 | Gomm et al. |
| 2010/0111765 A1 | 5/2010 | Gomm et al. |
| 2012/0222773 A1* | 9/2012 | Yamato .................. G01N 35/10 141/1 |
| 2013/0065797 A1* | 3/2013 | Silbert ............... G01N 35/0099 506/39 |
| 2015/0251173 A1* | 9/2015 | Maslana ................. B01L 3/021 422/509 |
| 2016/0178654 A1 | 6/2016 | Silbert et al. |

FOREIGN PATENT DOCUMENTS

| | | |
|---|---|---|
| EP | 2413136 A1 | 2/2012 |
| EP | 2261676 A1 | 12/2012 |
| WO | 2013148866 A1 | 10/2013 |
| WO | 2013185794 A1 | 10/2013 |

\* cited by examiner

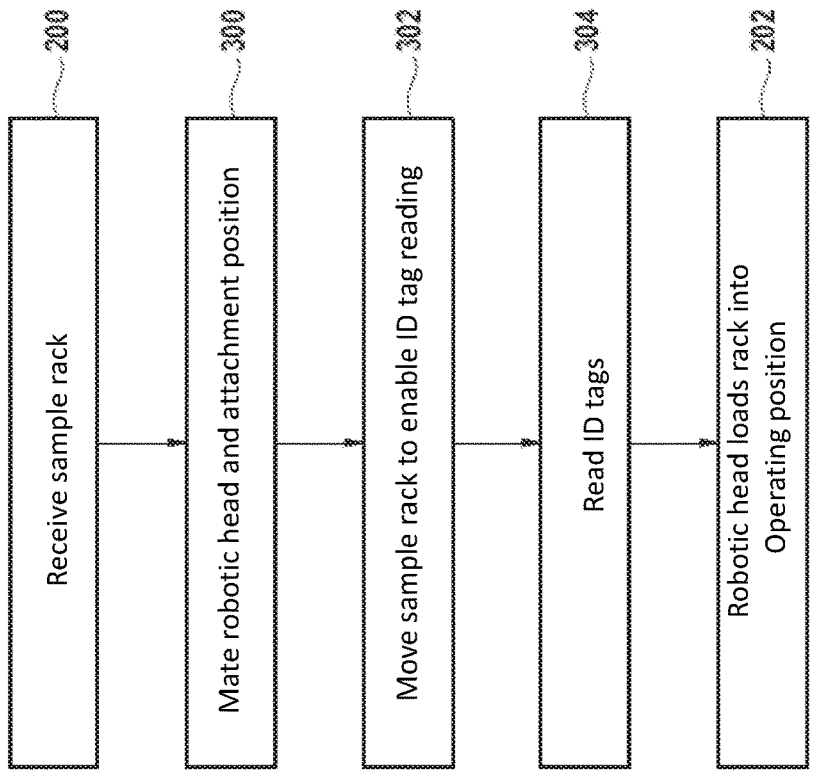
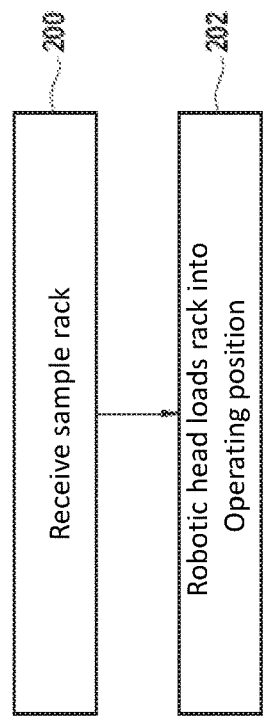

LABORATORY INSTRUMENT AND METHOD OF USING THE SAME

CROSS-REFERENCE TO RELATED APPLICATIONS

This application claims priority to European Patent Application No. 15197007.6, filed Nov. 30, 2015, the disclosure of which is incorporated herein by reference in its entirety.

TECHNICAL FIELD

The application relates to a laboratory instrument and a method of operating a laboratory instrument.

BACKGROUND AND RELATED ART

In vitro diagnostic testing has a major effect on clinical decisions, providing physicians with pivotal information. Particularly, there is great emphasis on providing quick and accurate test results in critical care settings.

One field of diagnostic testing is conducted with large laboratory instruments in clinical laboratories. Laboratory instruments are apparatuses that may be incorporated into manual or automated laboratories. Laboratory instruments encompass analytical devices such as analyzers and also pre/post-analytical instruments for processing biological samples. Biological samples may be placed into sample tubes which are then placed into sample racks that are loaded into the laboratory instrument. The sample tubes and/or the racks may have tags which are read by an identification tag reader such as a barcode label. A "sample rack" is a carrier, typically made of plastics and/or metal, adapted for receiving, holding and transporting one or more sample tubes, e.g., 5 or more sample tubes e.g., disposed in one or more rows. Apertures, windows or slits may be present to enable visual or optical inspection or reading of the sample tubes or of the samples in the sample tubes or of a label, such as a barcode, present on the sample tubes held in the sample rack.

The loading of sample racks into the laboratory instruments is a common task in a laboratory workflow which requires a certain degree of precision. For example, in order to enable identification tags on the sample tubes loading in the rack to be read by the laboratory instrument, the sample rack must be loaded substantially at a defined pace and/or in a defined direction and/or to a defined insertion depth. Manual loading of sample racks onto laboratory instruments is a task which is prone to errors, where the required precision is not observed. These errors might be due to operator fatigue, lack of attention, and/or very precise requirements.

Laboratory instruments comprising a sample rack loading means, in particular, automated sample rack loading mechanisms, are known in the art. However providing an automated sample loading mechanism for a laboratory instrument is not always feasible as it adds a significant amount of complexity and cost, and it can also add to the size to the laboratory instrument.

SUMMARY

Embodiments of the disclosed method for operating a laboratory instrument and the disclosed laboratory instrument aim at providing a solution to load sample racks, ensuring a required level of loading precision is maintained, thereby avoiding the disadvantages associated with known sample rack loading mechanisms.

Embodiments of the disclosed method/system load the sample racks into an operating position using the same robotic head, which comprises a pipettor of the laboratory instrument. Embodiments of the disclosed method/system are advantageous as the already existing robotic head with the pipettor is "reused" to load sample racks onto the laboratory instruments. Thus, a high precision of sample rack loading can be achieved without the need for complex additional hardware such as a dedicated automated sample rack loading mechanism.

Further embodiments of the disclosed method/system aim to load sample racks into an operating position within a laboratory instrument using the robotic head such as to enable an identification tag reader to read the tube identification tag.

BRIEF DESCRIPTION OF THE DRAWINGS

Certain embodiments are explained in greater detail, by way of example only, making reference to the drawings in which:

FIG. 2 shows a flow chart that illustrates a method of operating the laboratory instrument of FIG. 1.

FIG. 3 shows a flow chart that illustrates a further method of operating the laboratory instrument of FIG. 1.

FIG. 5B shows a detailed view of the mechanism shown in FIG. 5A.

FIG. 7B shows a detailed view of the mechanism shown in FIG. 7A.

DETAILED DESCRIPTION

Figure 1:
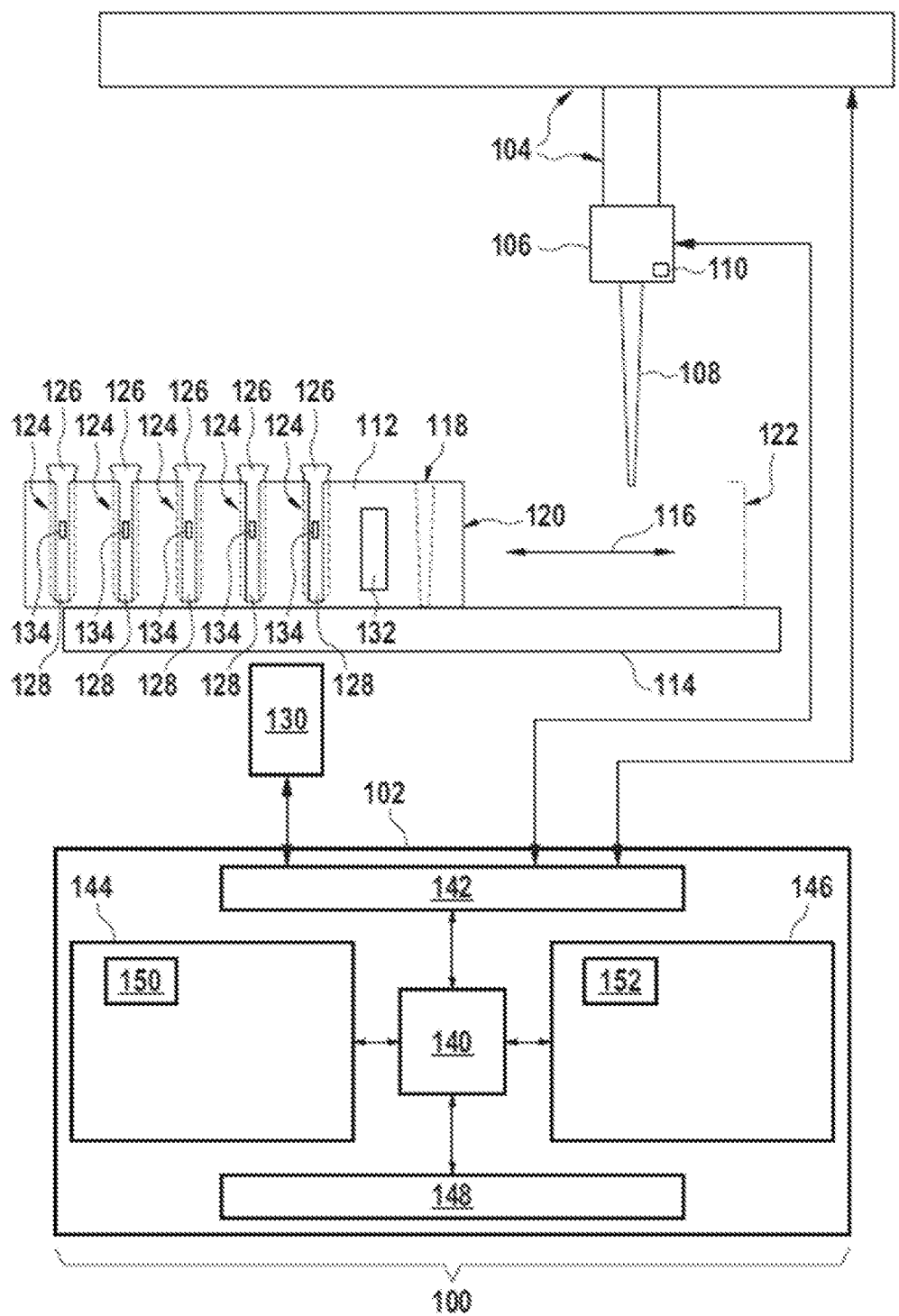
FIG. 1 illustrates an example of a laboratory instrument.

Like numbered elements referenced in the figure are either equivalent elements or perform the same function. Elements which have been discussed previously will not necessarily be discussed in later figures if the function is equivalent.

A "control unit" controls an automated or semi-automated system in a way that the necessary steps for the processing protocols are conducted by the automated system. That means the control unit may, for example, instruct the automated system to conduct certain pipetting steps to mix the liquid biological sample with reagents, or the control unit controls the automated system to incubate the sample mixtures for a certain time etc. The control unit may receive information from a data management unit regarding which steps need to be performed with a certain sample. In some embodiments, the control unit might be integral with the data management unit or may be embodied by a common hardware. The control unit may, for instance, be embodied as a programmable logic controller running a computer-readable program provided with instructions to perform operations in accordance with a process operation plan. The control unit may be set up to control, for example, any one or more of the following operations: loading and/or wasting and/or washing of cuvettes and/or pipette tips, moving and/or opening of sample tubes and reagent cassettes, pipetting of samples and/or reagents, mixing of samples and/or reagents, washing pipetting needles or tips, washing mixing paddles, controlling of a light source, e.g., selection of the wavelength, or the like. In particular, the control unit may include a scheduler for executing a sequence of steps within a predefined cycle time. The control unit may further determine the order of samples to be processed according to the assay type, urgency, and the like.

As mentioned above a "laboratory instrument" may include analyzers and/or pre/post-analytical instruments for processing biological samples. A biological sample as used herein encompasses any chemical product derived, copied, replicated, or reproduced from a sample taken from an organism. An analyzer, as used herein, encompasses an apparatus that makes a measurement on a biological sample to determine a physical characteristic or property of the biological sample.

In one aspect, embodiments of the invention provide for a method of operating a laboratory instrument. The laboratory instrument is configured for receiving a sample rack with one or more sample tubes. The laboratory instrument comprises a robotic head for bringing a pipettor into fluidic contact with the one or more sample tubes when the sample rack is in an operating position. The robotic head is configured for loading the sample rack into the operating position. The method comprises the step of receiving the sample rack by the laboratory instrument. The method further comprises loading the rack into the operating position using the robotic head. This embodiment may have the benefit that the robotic head is used for both loading the rack into the operating position and also for moving the pipettor into fluidic contact with the one or more sample tubes when in an operating position.

In another embodiment, the laboratory instrument comprises an identification tag reader. The one or more sample tubes have a tube identification tag. The sample rack is loaded by the robotic head into the operating position such as to enable an identification tag reader to read the tube identification tag. This embodiment may have the benefit that the robotic head can manipulate the sample rack such that the identification tag reader can conveniently read the tube identification tag.

In another embodiment, the sample rack comprises an attachment position. The pipettor is configured for mating with the attachment position of the sample rack. The sample rack further comprises multiple sample tube receptacles. Each sample tube receptacle is configured for receiving the one or more sample tubes. The laboratory instrument comprises an input guide for receiving the sample rack. The input guide is configured for receiving the sample rack along an insertion direction. The input guide has an opening. The step of receiving the sample rack by the laboratory instrument comprises at least partially receiving the sample rack into the input guide along the insertion direction.

The method further comprises the step of controlling the robotic head to mate with the attachment position of the sample rack. The method further comprises the step of controlling the robotic head to move the sample rack in the input guide along the insertion direction such as to enable the tube identification tag to be read by the identification tag reader. The method further comprises the step of reading the tube identification tag with the identification tag reader as the sample rack is moved in the input guide. This may be useful as an aide when manually placing the sample rack on or into the input guide.

In another embodiment, the insertion slot has a first optically visible marking. The sample rack has a second optically visible marking. The step of at least partially receiving the sample rack into the input guide along the insertion direction is performed such as that the first optically visible marking is substantially aligned with the second optically visible marking.

In another embodiment, the method further comprises the step of controlling the robotic head to move the pipettor in the input guide. The pipettor is moved in the input guide along the insertion direction from a starting position towards the opening. The method further comprises the step of detecting a contact event between the pipettor and an insertion end of the rack using the contact detector. The method further comprises the step of controlling the robotic head to halt movement in the insertion direction when a contact event is detected.

In another embodiment, the method further comprises the step of controlling the robotic head to move the sample rack partially out of the input guide to position the sample rack to a predefined insertion depth.

In another embodiment, the laboratory instrument further comprises a hinged lid for covering the opening of the input guide. The hinged lid is configured for being in an open position and a closed position. When in the open position the hinged lid is configured for supporting the sample rack during insertion into the input guide.

In another embodiment, the pipettor is any one of the following: a pipetting head, a sample head, and a reagent head.

In another aspect, the invention provides for a laboratory instrument. The laboratory instrument is configured for receiving a sample rack with one or more sample tubes. The laboratory instrument comprises a robotic head for bringing a pipettor into fluidic contact with the one or more sample tubes when the sample rack is in an operating position. The robotic head is configured for loading the sample rack into the operating position.

In another embodiment, the laboratory instrument comprises an identification tag reader. At least a portion of the one or more sample tubes has a tube identification tag. The sample rack is loaded into the operating position by the robotic head such as to enable the identification tag reader to read the tube identification tag.

In another embodiment, the laboratory instrument further comprises an input guide for receiving a sample rack. The input guide is configured for receiving the sample rack along an insertion direction. The input guide has an opening. The sample rack further comprises multiple sample tube receptacles. Each sample tube receptacle is configured for receiving a sample tube with a sample tube identification tag. The step of receiving the sample rack with the laboratory instrument comprises at least partially receiving the sample rack into the input guide along the insertion direction.

The laboratory instrument further comprises a control unit for controlling the laboratory instrument. The controller is configured to control the robotic head to mate with an attachment position of the sample rack. The control unit is further comprised for controlling the robotic head to move the sample rack in the input guide along the insertion direction to enable the tube identification tag to be read by the identification tag reader. The control unit is further configured to read the tube identification tag with the identification tag reader as the sample rack is moved into the input guide.

In another embodiment, the robotic head is configured for moving the pipettor in the input guide along the insertion direction.

In another embodiment, the attachment position is located at an insertion end of the rack.

In another embodiment, the laboratory instrument comprises a contact detector for detecting contact between the pipettor and the insertion end of the rack. The controller is configured to control the robotic arm to move the pipettor in the input guide. The pipettor is moved in the input guide along the insertion direction from the starting position towards the opening. The controller is further configured for detecting a contact event between the pipettor and an insertion end of the rack using the contact detector. The controller is further configured to control the robotic arm to halt movement in the insertion direction when the contact event is detected.

In another embodiment, the controller is further configured for controlling the robotic head to move the sample rack partially out of the input guide to position the sample rack to a predetermined insertion depth.

In another embodiment, the contact detector is any one of the following: a contact switch, a force sensing transducer in contact with the pipettor, and a current or voltage sensor on a motor of the robotic head.

In another embodiment, the laboratory instrument further comprises a hinged lid for covering the opening of the input guide. The hinged lid is configured for being in an open position and a closed position. When in an open position the hinged lid is configured for supporting the sample rack during insertion into the input guide.

In another embodiment, the identification tag reader comprises any one of the following: a barcode reader, an RFID reader, and combinations thereof.

In embodiment identification tag is a barcode and/or an RFID or combinations thereof.

In another aspect, the invention provides for a computer program product comprising machine-executable code for execution by a controller for a laboratory instrument. The laboratory instrument is configured for receiving a sample rack with one or more sample tubes. Execution of the machine-executable code causes the controller to control the robotic head to load the sample rack into an operating position. Execution of the machine-executable code further causes the controller to control the robotic head to bring a pipettor into fluidic contact with the one or more sample tubes when the sample rack is in an operating position.

Further disclosed is a computer program including computer-executable instructions for performing the method according to the present invention in one or more of the embodiments enclosed herein when the program is executed on a computer or computer network operatively connected to the laboratory instrument. Specifically, the computer program may be stored on a computer-readable data carrier. Thus, specifically, one, more than one or even all of method steps as indicated above may be performed by using a computer or a computer network, preferably by using a computer program.

Further disclosed is a computer program product having program code means, in order to perform the method according to the present invention in one or more of the embodiments enclosed herein when the program is executed on a computer or computer network. Specifically, the program code means may be stored on a computer-readable data carrier.

Further disclosed is a data carrier having a data structure stored thereon, which, after loading into a computer or computer network, such as into a working memory or main memory of the computer or computer network, may execute the method according to one or more of the embodiments disclosed herein.

Further disclosed is a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Further disclosed is a modulated data signal which contains instructions readable by a computer system or computer network, for performing the method according to one or more of the embodiments disclosed herein.

Referring to the computer-implemented aspects of the invention, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

FIG. 1 shows an example of part of a laboratory instrument 100. The laboratory instrument is shown as containing a controller 102. The laboratory instrument 100 further comprises a robotic arm 104 that is used for manipulating a robotic head 106. The robotic head 106 is connected to a pipettor 108. The pipettor can be used for either dispensing a fluid or manipulating a fluid in some other way such as performing a pipetting operation. The pipettor 108 is shown as having an optional contact detector 110. The contact detector 110 can be used to detect when the pipettor 108 contacts or hits an object. The laboratory instrument 100 is further shown as having a sample rack 112 that has been loaded into an insertion guide 114. The sample rack 112 is able to be inserted along an insertion direction 116 along the insertion guide 114.

The sample rack 112 is shown as having an attachment position 118 where the pipettor 108 is able to be placed into or locked into the sample rack 112. The sample rack 112 has an insertion end 120 which is placed first along the insertion guide 114. The sample rack 112 can be inserted along the insertion guide 114 up to an operating position 122. When the insertion end 120 is at the line labeled 122 the sample rack 112 is in the operating position. The sample rack 112 is shown as containing a number of sample tube receptacles 124. The sample tube receptacles 124 are shown as holding individual sample tubes 126. The sample rack 112 is shown as having optional openings 128. The openings 128 are spaces which have been cut or formed in the sample rack 112 such that it enables visual inspection of the sides of the sample tubes 126. The openings 128 are optional features and may be useful if it is desired to optically inspect the sides of the sample tubes 126.

The laboratory instrument 100 is further shown as containing an identification tag reader 130. The sample rack 112 is shown as having an optional rack identification tag 132 that can be read by the identification tag reader 130 to identify a particular sample rack 112. The sample tubes 126 are shown as having tube identification tags 134. The tube identification tags may be used to identify individual sample tubes 126 using the identification tag reader 130. In some examples the identification tag reader 130 is a barcode reader and the tags 134, 132 are read optically. In other examples the identification tag reader 130 reads the tags 132, 134 via electromagnetic means for example the identification tag reader could be an RFID tag reader. In other examples the identification tag reader 130 is able to read both optical and RFID tags. In this case the tags 132 and 134 may be barcode and/or RFID tags.

When the identification tag reader 130 is an optical tag reader it may be desirable to use a low cost barcode reader. Low cost barcode readers may rely on a barcode being positioned properly and also not being moved too rapidly past the barcode reader. For example, so called line scan cameras are inexpensive, but they rely on the barcode being moved past the line scan camera within a predetermined velocity range.

In one example the pipettor 108 could be used to first detect the position of the sample rack 112 by moving the pipettor 108 along the insertion direction 116 until it contacts the insertion end 120. This may be detected using the contact detector 110. After this happens the position of the insertion end 120 is precisely known. The robotic head 106 can then move the pipettor 108 so that it mates with the attachment position 118. The robotic head 106 can then move the sample rack 112 to a starting position and then move the sample rack 112 into a position or at a slow enough velocity so that the identification tag reader 130 can read the rack identification tag 132. The robotic head 106 may then move the pipettor 108 further along the insertion direction 116 such that all of the tube identification tags 134 can be read by the identification tag reader 130.

The controller 102 is shown as containing a processor 140. The processor 140 is connected to a hardware interface 142. The hardware interface 142 is connected to the identification tag reader 130, the robotic head 106 and the robotic arm 104. The hardware interface 142 enables the processor 140 to control these components. The processor 140 is further shown as being connected to a storage 144, memory 146, and a user interface 148. The laboratory instrument 100 may also contain one or more measurement instruments. The computer storage 144 may for example contain measurement data 150. The computer memory 146 is shown as containing machine-executable instructions 152. The machine-executable instructions 152 may enable the processor 140 to control and operate the other components of the laboratory instrument.

FIG. 2 shows a flowchart which illustrates an example of a method of operating the laboratory instrument 100 of FIG. 1. First in step 200 the sample rack 112 is received by the laboratory instrument 100. Next in step 202 the robotic head 106 loads the rack 112 into the operating position 122.

FIG. 3 shows a flowchart which illustrates further details of the method illustrated in FIG. 2. The method shown in FIG. 3 starts with step 200 as is illustrated in FIG. 2. Next in step 300 the robotic head 106 is controlled to mate with the attachment position 118 of the sample rack 112. For example, the pipettor 108 is moved into the attachment position 118. In other examples the robotic head could change to a rigid finger or other device which is used to mate with the sample rack 112. Next in step 302 the robotic head is controlled to move the sample rack in an input guide 114 along the insertion direction 116 such as to enable the tube identification tags 134 to be read by the identification tag reader 130. Next in step 304 the tube identification tags 134 are read with the identification tag reader as the sample rack is moved in the input guide 114 along the input direction 116. Finally the method shown in FIG. 3 ends with step 202 as is illustrated in FIG. 2.

FIGS. 4-9 illustrate a method of operating the laboratory instrument 100 of FIG. 1 graphically.

Figure 4:
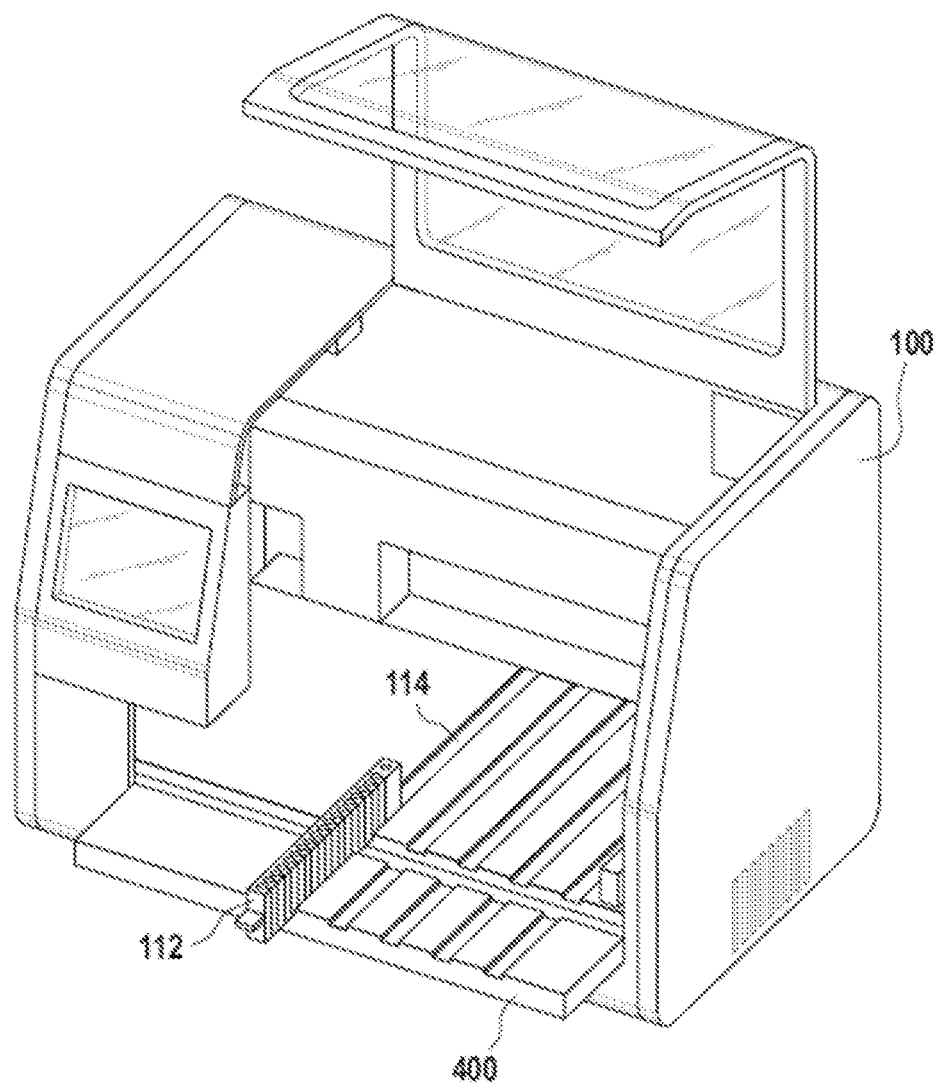
FIG. 4 shows a representation of a laboratory instrument that partially illustrates a method.

In FIG. 4 a depiction of a laboratory instrument 100 is seen. In this example the laboratory instrument 100 has a hinged lid 400 that can be flipped down and aids in supporting the sample rack 112 when it is partially inserted into the insertion guide 114. In FIG. 4 it can be seen that a sample rack 112 has been partially inserted into the insertion guide 114.

Figure 5A:
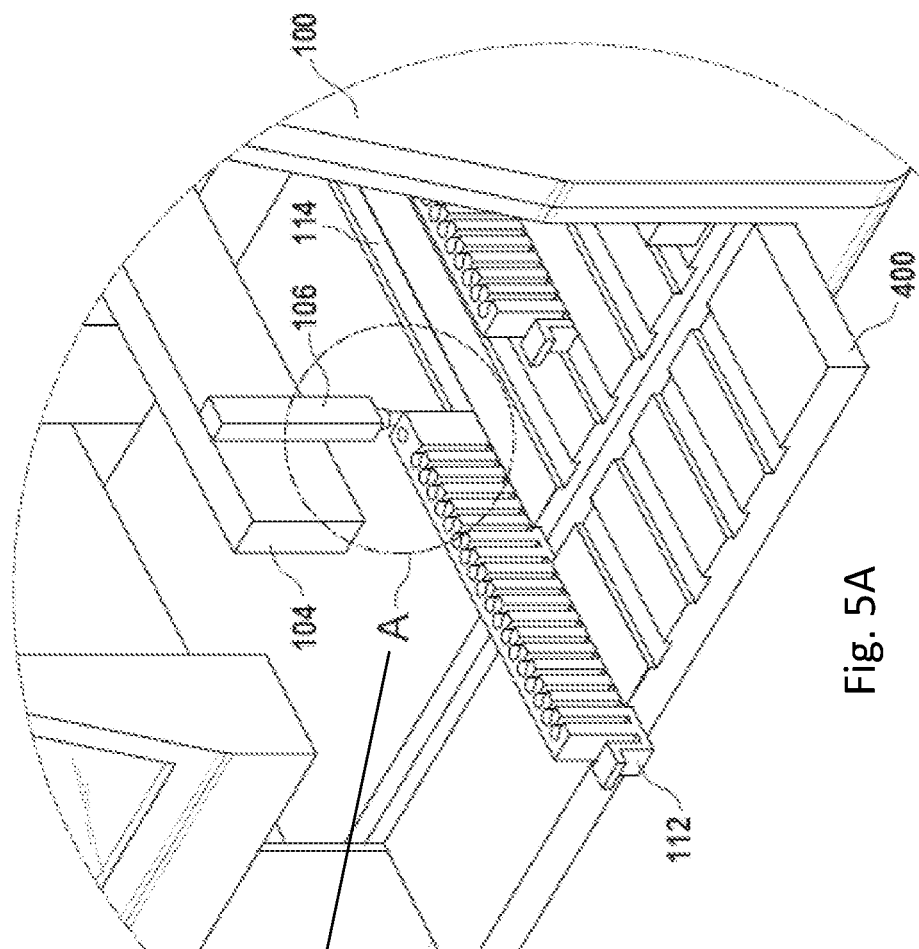
FIGS. 5A-5B show a representation of a laboratory instrument which further illustrates the method of FIG. 4.
Figure 5B:
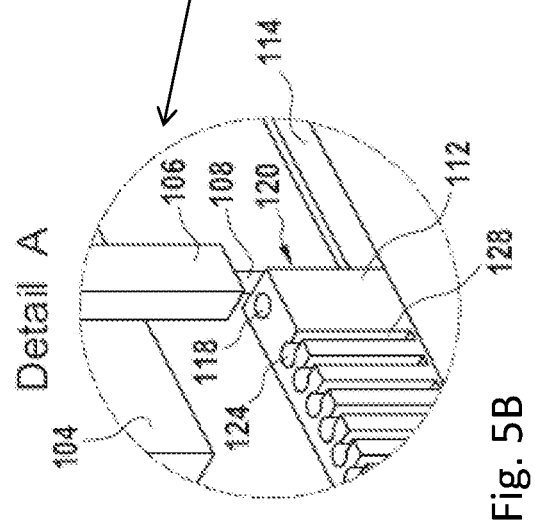
Figure 6:
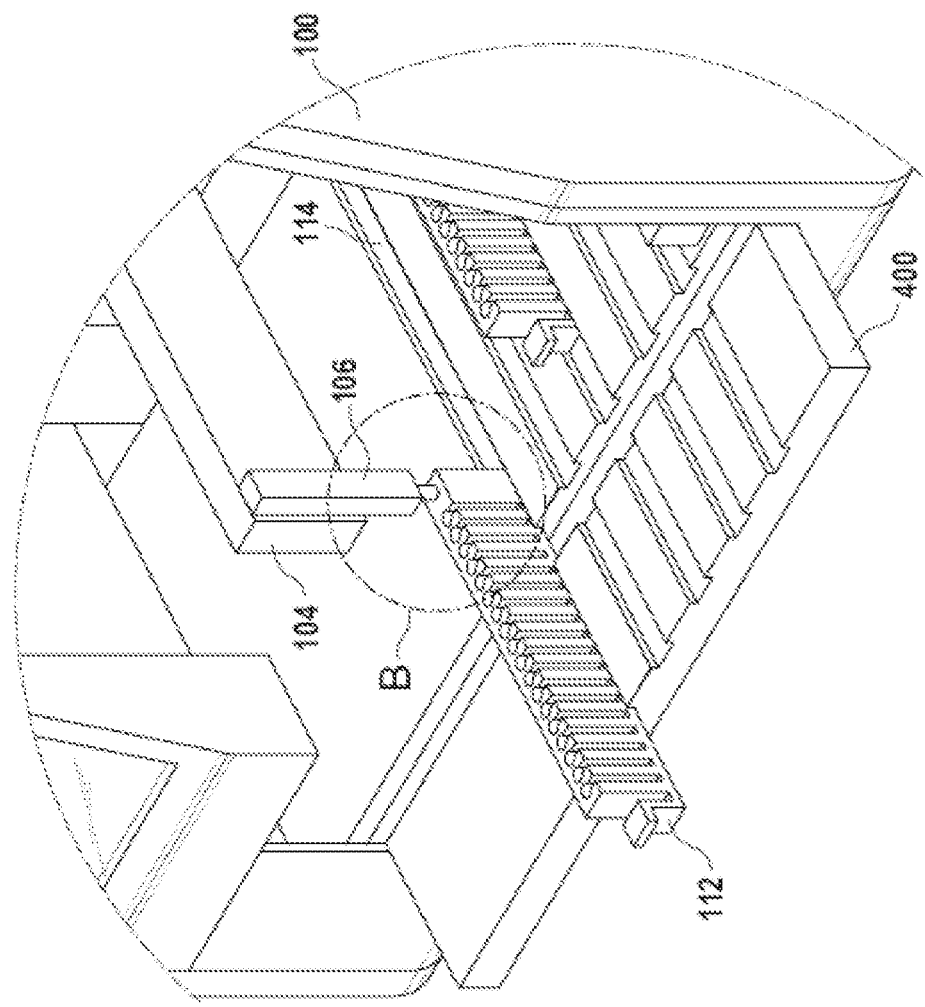
FIG. 6 shows a representation of a laboratory instrument which further illustrates the method of FIGS. 4 to 5.

Next in FIG. 5(*a*), the robotic head 106 moves the pipettor 108 along the insertion direction which is essentially parallel to the insertion guide 114. The robotic head 106 moves the pipettor 108 until it contacts the sample rack 112. This is done to identify the location of the sample rack 112. In FIG. 5(*b*) it can be seem that the pipettor 108 contacts the insertion end 120 of the sample rack 112. Next in FIG. 6 it can be seen that the robotic head 106 has used the pipettor 108 to push the sample rack 112 further out of the laboratory instrument 100 along the insertion guide 114. This may be done for example to position the sample rack 112 such that any identification tags on the rack 112 or on sample tubes may be read efficiently by a identification tag reader 130. The identification tag reader 130 is not shown in the example illustrated in FIGS. 4-9. As an alternative to what is shown in FIG. 5 the robotic head 106 may move the pipettor to mate with the attachment position 118 before the sample rack 112 is moved partially out of the laboratory instrument 100.

Figure 7A:
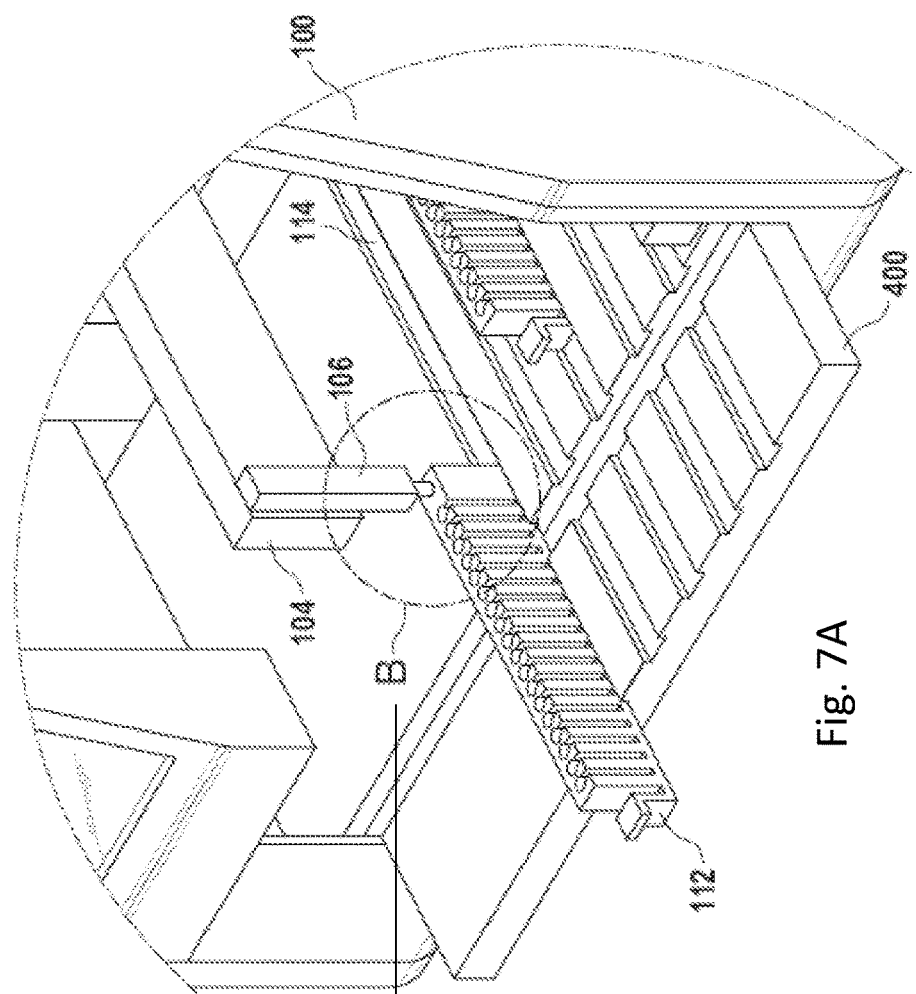
FIGS. 7A-7B show a representation of a laboratory instrument which further illustrates the method of FIGS. 4 to 6.
Figure 7B:
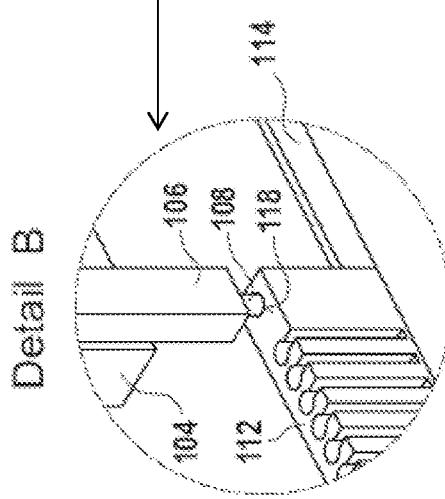

In FIG. 7(*a*)-(*b*) the robotic head 106 is used to control and move the pipettor 108 such that it is positioned into and mates with the attachment position 118. With the pipettor 108 in the attachment position 118 the robotic head 106 is then able to pull the sample rack 112 back along the insertion direction and along the insertion guide 114 into the laboratory instrument 100.

Figure 8:
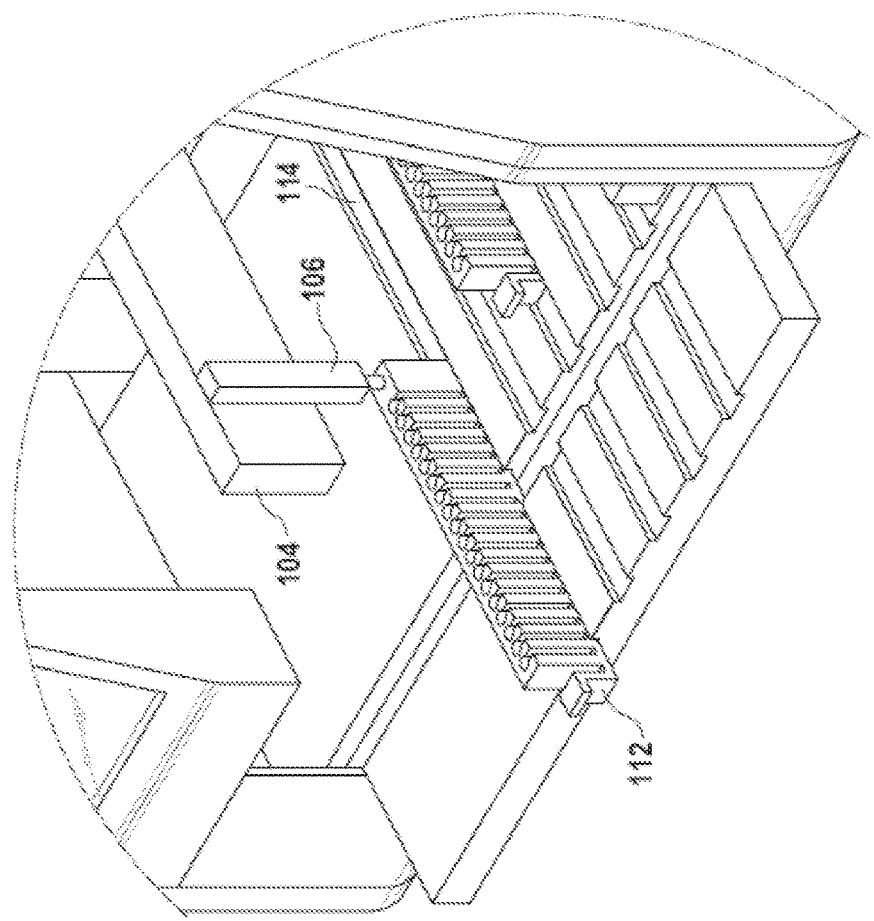
FIG. 8 shows a representation of a laboratory instrument which further illustrates the method of FIGS. 4 to 7.

FIG. 8 shows the sample rack 112 in an intermediate position before it has been pulled into the operating position 122. This intermediate position, for example, may be at a location where any tags on the rack 112 and/or sample tubes may be read by the identification tag reader 130.

Figure 9:
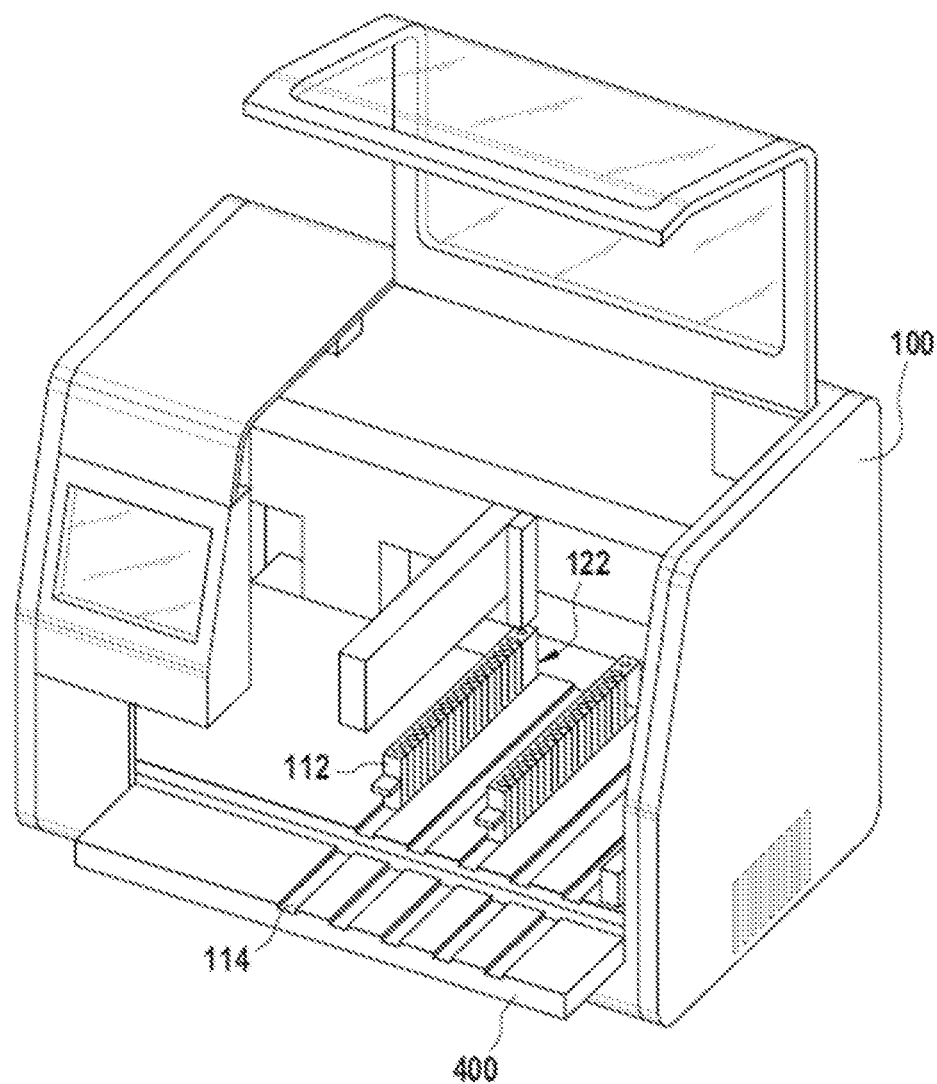
FIG. 9 shows a representation of a laboratory instrument which further illustrates the method of FIGS. 4 to 8.

FIG. 9 shows the sample rack 112 after it has been withdrawn all the way into the laboratory instrument 100 along the insertion guide 114. The sample rack 112 is now in an operating position 122.

Figure 10:
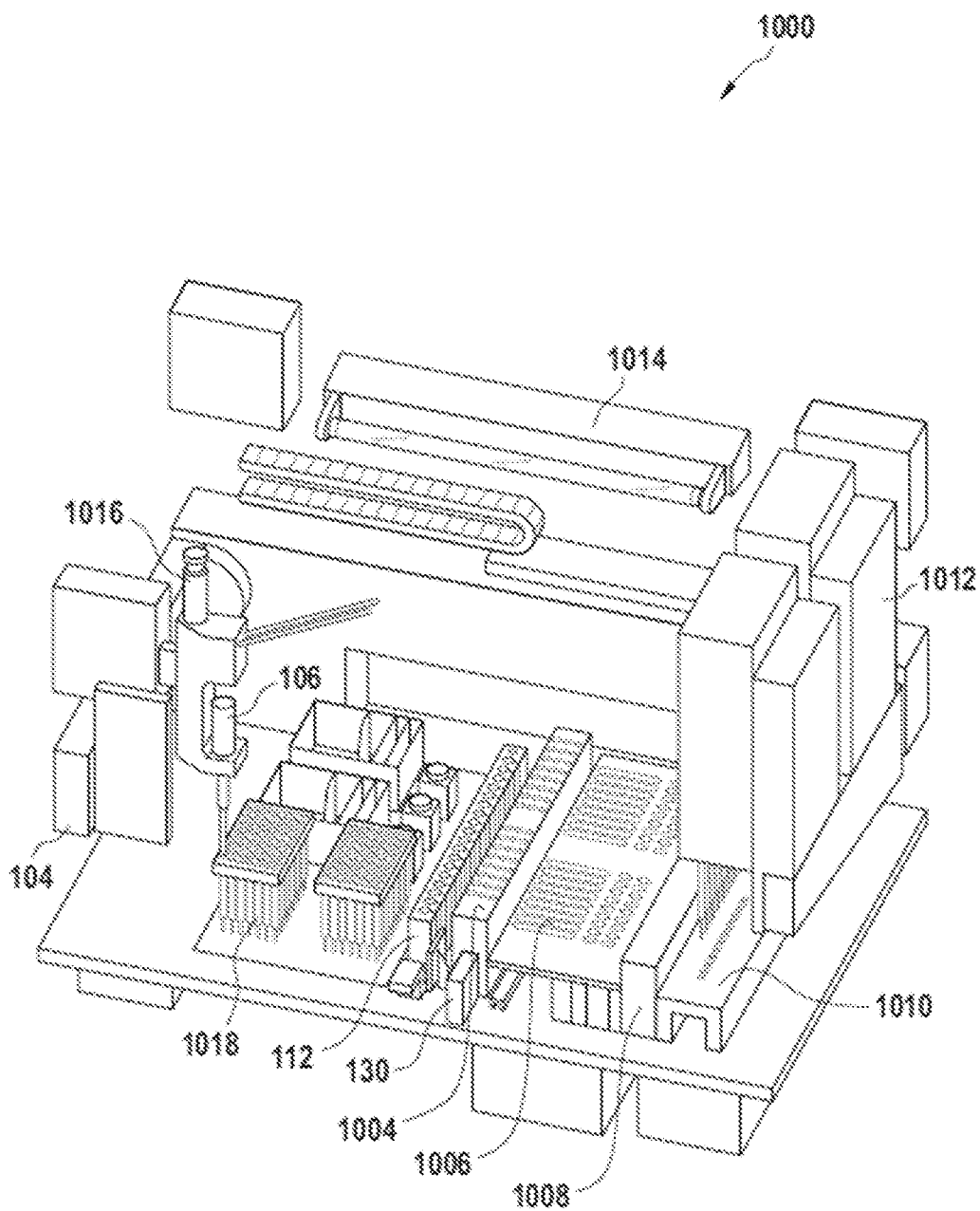
FIG. 10 shows an assembly drawing of a laboratory instrument.

The examples shown in FIG. 1 and in FIGS. 4-9 are simplified. FIG. 10 shows a more detailed example of a laboratory instrument 1000 that could be an implementation of a system such as depicted in FIG. 1. In FIG. 10 the cover of the laboratory instrument 1000 has been removed to show a number of components. In this example a sample rack 112 is shown. Adjacent to the sample rack is an identification tag reader 130. Also adjacent to the sample rack 112 is an automatic tip loading 1004 apparatus. Next to the automated tip loading station 1004 is a processing area 1006 and/or an area for receiving liquid waste. The region labeled 1008 is a region for accepting waste tips or tip waste. The region 1010 is a cooling station for eluate output. Element 1012 is a 16-fold processing head. Above this there is an ultraviolet lamp 1014. There is a sample or reagent head 1016 which is also indicated as being the robotic head 106. The sample or reagent head 1016 is attached to the robotic arm 104. FIG. 10 also shows the location of a reagent area 1018.

The laboratory instrument 1000 shown in FIG. 10 may be a reduced cost instrument, because the use of the robotic head may enable the use of a less expensive line scan camera as the identification tag reader.

Figure 11:
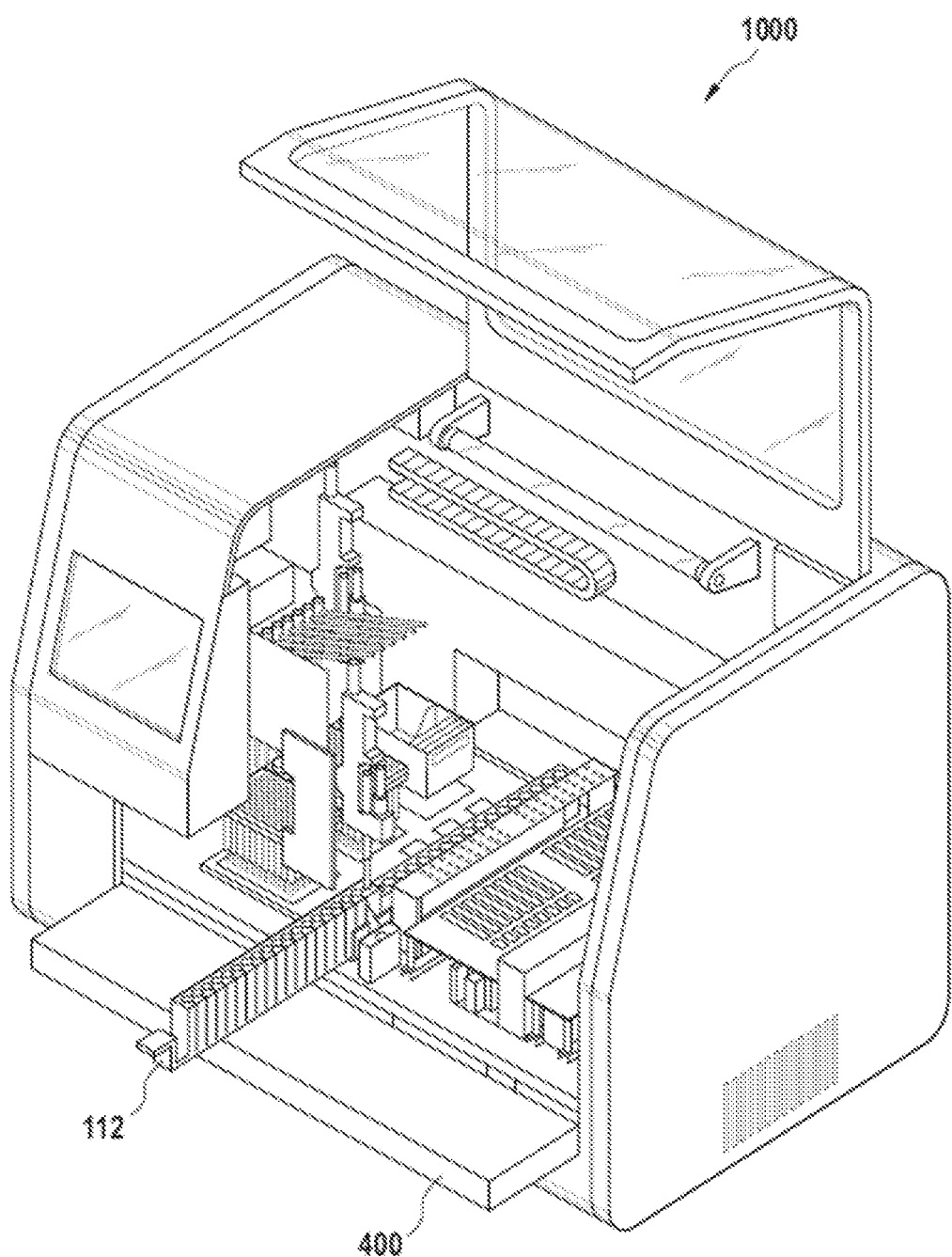
FIG. 11 shows a further assembly drawing of the laboratory instrument of FIG. 10.

FIG. 11 shows an assembly drawing of the laboratory instrument 1000. The view in FIG. 11 is equivalent to the view shown in FIG. 8.

Figure 12:
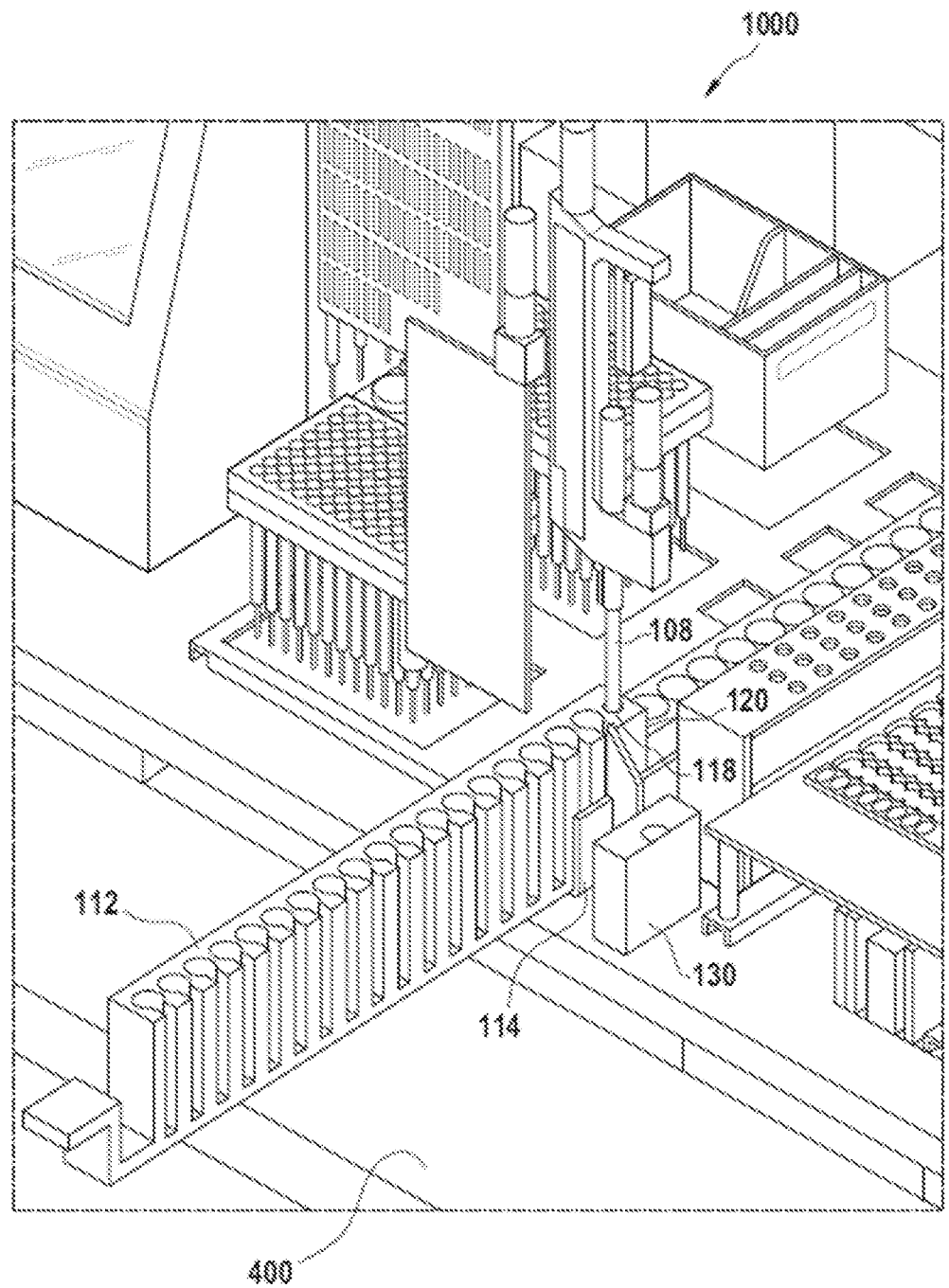
FIG. 12 shows a further assembly drawing of the laboratory instrument of FIG. 10.

FIG. 12 shows an enlarged view of FIG. 11 to show the sample rack 112 in greater detail. In FIG. 12 it can be seen that the insertion guide 114 is a curved piece of material for receiving the sample rack 112. Further it can be seen that the identification tag reader 130 is positioned for reading identification tags near the insertion end 120 of the sample rack 112.

Figure 13:
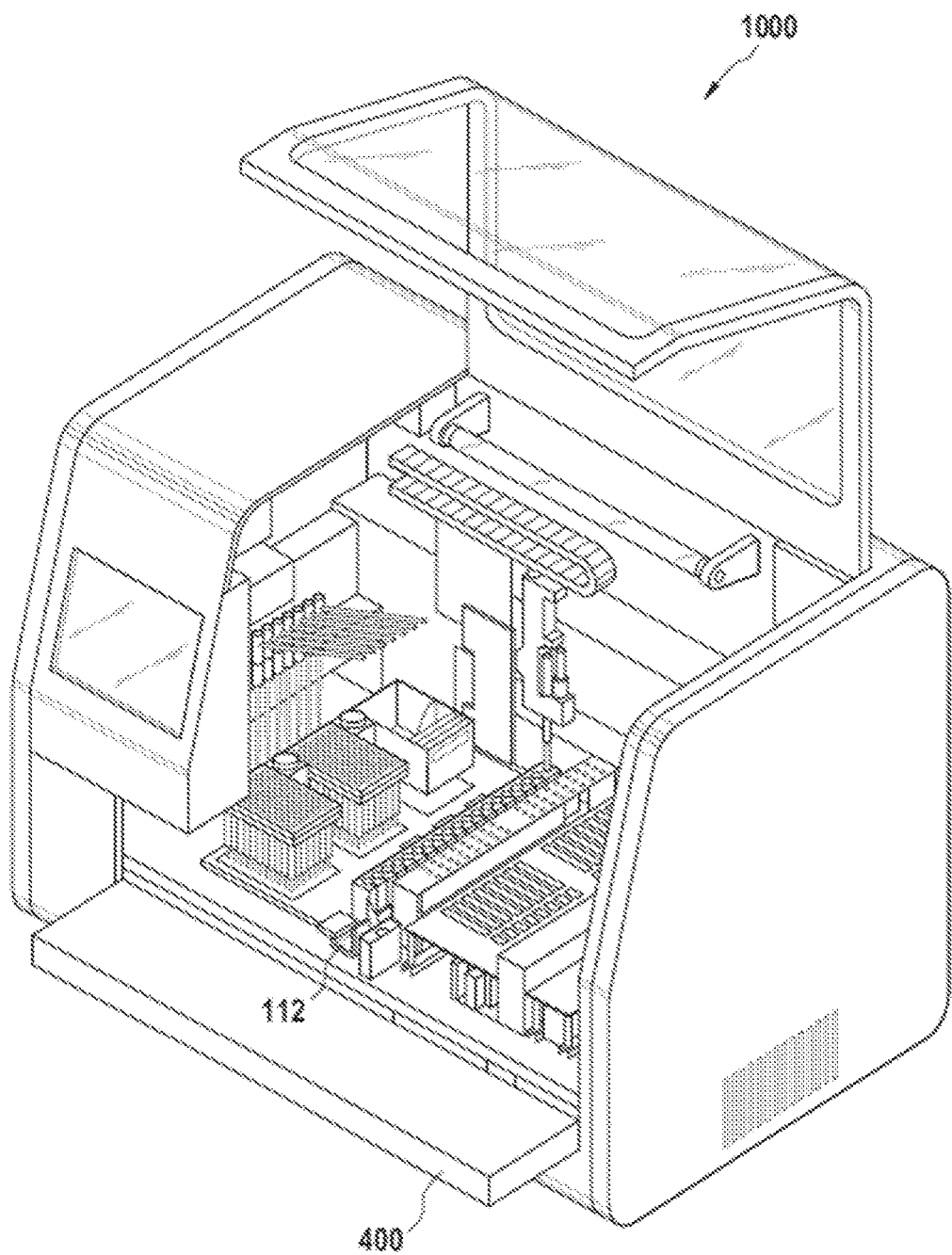
FIG. 13 shows a further assembly drawing of the laboratory instrument of FIG. 10.

FIG. 13 shows a further assembly drawing of the laboratory instrument 1000. The view shown in FIG. 13 is equivalent to the view shown in FIG. 9. The sample rack 112 has been placed into the operating position.

Figure 14:
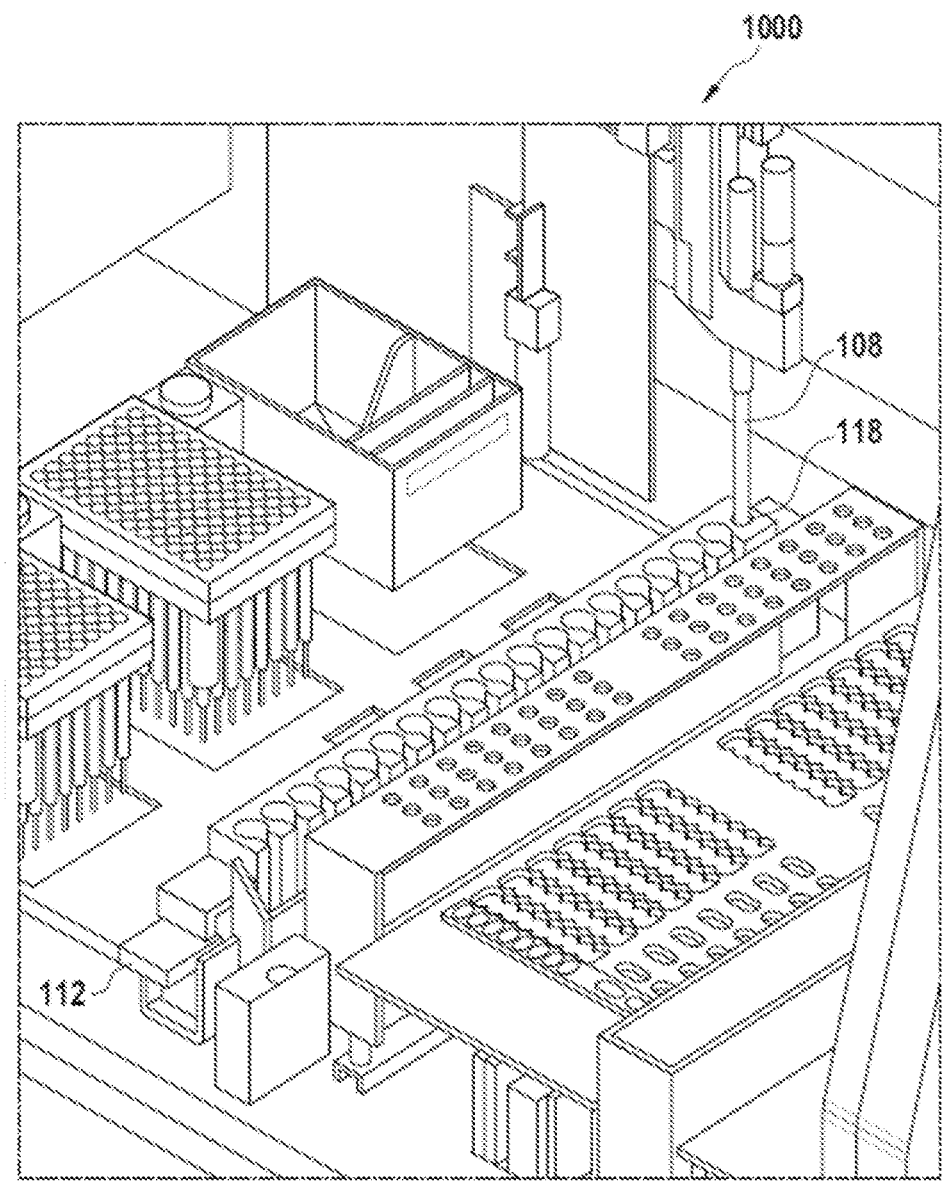
FIG. 14 shows a further assembly drawing of the laboratory instrument of FIG. 10.

FIG. 14 shows an enlarged view of FIG. 13 to show the sample rack 112 in greater detail. It can be seen that the pipettor 108 is still mated with the attachment position 118.

It is understood that one or more of the aforementioned embodiments of the invention may be combined as long as the combined embodiments are not mutually exclusive.

All patents, patent applications, publications, and descriptions mentioned here are incorporated by reference in their entirety for all purposes. None is admitted to be prior art.

LIST OF REFERENCE NUMERALS

100 Laboratory instrument
102 controller
104 robotic arm
106 robotic head
108 pipettor
110 contact detector
112 sample rack
114 insertion guide
116 insertion direction
118 attachment position
120 insertion end
122 operating position
124 sample tube receptacles
126 sample tube
130 identification tag reader
132 rack identification tag
134 tube identification tag
140 processor
142 hardware interface
144 storage
146 memory
148 user interface
150 measurement data
152 machine executable instructions
200 receiving the sample rack by the laboratory instrument
202 loading the rack into the operating position using the robotic head
300 controlling the robotic head to mate with the attachment position of the sample rack
302 controlling the robotic head to move the sample rack in the input guide along the insertion direction such as to enable the tube identification tag to be read by the identification tag reader
304 reading the tube identification tag with the identification tag reader as the sample rack is moved in the input guide
400 hinged lid
1000 laboratory instrument
1004 automated tip loading
1006 processing area/liquid waste
1008 tip waste
1010 cooling station (eluate output)
1012 16 fold processing head
1014 UV lamp
1016 sample/reagent head
1018 reagent area

The invention claimed is:

1. A method of operating a laboratory instrument, wherein the laboratory instrument is configured to receive a sample rack having one or more sample tubes, the laboratory instrument comprising a robotic head operably connected to a pipettor capable of being brought into fluidic contact with the one or more sample tubes when the sample rack is in an operating position in the laboratory instrument, wherein the laboratory instrument receives the sample rack along only one direction, an insertion direction, and wherein the method comprises the steps of:
   (a) receiving the sample rack by the laboratory instrument; and
   (b) loading, via the robotic head, the sample rack into the operating position.

2. The method of claim 1, wherein the laboratory instrument further comprises an identification tag reader and the one or more sample tubes have a tube identification tag, and loading step (b) further comprises loading the sample rack into the operating position to enable the identification tag reader to read the tube identification tag on the one or more sample tubes.

3. The method of claim 2, wherein the sample rack comprises an attachment position, wherein the pipettor is configured to mate with the attachment position and the laboratory instrument further comprises an insertion guide configured to receive the sample rack along the insertion direction in the laboratory instrument, the insertion guide having an opening, the method further comprising the steps of:
   (a) mating the robotic head with the attachment position;
   (b) moving, via the robotic head, the sample rack in the insertion guide along the insertion direction, to align the tube identification tag with the identification tag reader; and
   (c) reading, via the identification tag reader, the tube identification tag.

4. The method of claim 3, wherein an insertion slot has a first optically visible marking, wherein the sample rack has a second optically visible marking, wherein the step of moving the sample rack into the insertion guide along the insertion direction is performed such that the first optically visible marking is substantially aligned with the second optically visible marking.

5. The method of claim 4, wherein the moving step (b) further comprises the steps of:
   controlling the robotic head to move the pipettor in the insertion guide along the insertion direction from a starting position towards the opening;

detecting a contact event between the pipettor and an insertion end of the sample rack using a contact detector; and controlling the robotic head to halt movement in the insertion direction when a contact event is detected.

6. The method of claim 5, further comprising the step of controlling the robotic head to move the sample rack partially out of the insertion guide to position the sample rack to a predefined insertion depth.

7. A laboratory instrument configured to receive a sample rack with one or more sample tubes, wherein the laboratory instrument comprises an insertion guide configured to receive the sample rack along a only one direction, an insertion direction, and wherein a robotic head operably connected to a pipettor and configured to (a) load the sample rack into an operating position within the laboratory instrument, and (b) bring the pipettor into fluidic contact with the one or more sample tubes when the sample rack is in an operating position.

8. The laboratory instrument of claim 7, wherein the laboratory instrument further comprises an identification tag reader and the one or more sample tubes have a tube identification tag, and the identification tag reader is configured to read the tube identification tags on each of the one or more sample tubes when wherein the sample rack is loaded into the operating position.

9. The laboratory instrument of claim 8, wherein the sample rack further comprises multiple sample tube receptacles, wherein each sample tube receptacle is configured to receive a sample tube having a sample tube identification tag.

10. The laboratory instrument of claim 8, wherein the laboratory instrument further comprises a control unit and the sample rack comprises an attachment position, wherein the control unit is configured to (a) control the robotic head to mate with the attachment position; (b) control the robotic head to move the sample rack in the insertion guide along the insertion direction to enable the tube identification tag to be read by the identification rag reader; and (c) read the tube identification tag with the identification tag reader as the sample rack is moved into the insertion guide.

11. The laboratory instrument of claim 8, wherein the robotic head is configured to move the pipettor in the insertion guide along the insertion direction.

12. The laboratory instrument of claim 11, wherein the laboratory instrument further comprises a contact detector for detecting contact between the pipettor and an insertion end of the sample rack, wherein the controller is configured to: (a) control the robotic arm to move the pipettor in the insertion guide, wherein the pipettor is moved in the insertion guide along the insertion direction from a starting position towards the opening; (b) detect a contact event between the pipettor and an insertion end of the sample rack using the contact detector; and (c) control the robotic arm to halt movement in the insertion direction when the contact event is detected.

13. The laboratory instrument of claim 10, wherein the control unit is further configured to control the robotic head to move the sample rack at least partially out of the insertion guide to position the sample rack to a predefined insertion depth.

14. The laboratory instrument of claim 8, further comprising a hinged lid to cover the opening of the insertion guide, wherein the hinged lid is configured to be in an open position and a closed position, and when the hinged lid is in the open position, the hinged lid can support the sample rack during insertion into the insertion guide.

15. The laboratory instrument of claim 8, wherein the identification tag reader comprises a bar code reader, an RFID reader, or combinations thereof, and correspondingly, the tube identification tag comprises a bar code and RFID tag or combinations thereof.

16. A computer program product comprising machine executable code for execution by a controller for a laboratory instrument, wherein the laboratory instrument comprises an insertion guide configured to receive a sample rack along only one direction, an insertion direction, in the laboratory instrument, and wherein the sample comprises one or more sample tubes and the controller is configured to (a) control a robotic head to load the sample rack into an operating position in the laboratory instrument; and (b) control a robotic head to bring a pipettor into fluidic contact with the one or more sample tubes when the sample rack is in the operating position.

* * * * *